United States Patent
Jensen et al.

(10) Patent No.: US 9,381,257 B2
(45) Date of Patent: Jul. 5, 2016

(54) TRIARYLMETHYL RADICALS

(71) Applicant: BRACCO IMAGING S.P.A., Milan (IT)

(72) Inventors: Pernille Rose Jensen, Vaerlose (DK); Magnus Karlsson, Malmo (SE); Mathilde H. Lerche, Frederiksberg C (DK); Roberta Napolitano, Albiano D'Ivrea (IT); Fabio Tedoldi, Marzano (IT); Massimo Visigalli, Settala (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 14/414,224

(22) PCT Filed: Jul. 4, 2013

(86) PCT No.: PCT/EP2013/064121
§ 371 (c)(1),
(2) Date: Jan. 12, 2015

(87) PCT Pub. No.: WO2014/009240
PCT Pub. Date: Jan. 16, 2014

(65) Prior Publication Data
US 2015/0151009 A1    Jun. 4, 2015

(30) Foreign Application Priority Data

Jul. 13, 2012 (EP) .................................... 12176269

(51) Int. Cl.
*A61K 49/10* (2006.01)
*A61K 49/20* (2006.01)
*C07F 7/08* (2006.01)
*G01R 33/28* (2006.01)

(52) U.S. Cl.
CPC ................. *A61K 49/10* (2013.01); *A61K 49/20* (2013.01); *C07F 7/0812* (2013.01); *C07F 7/0814* (2013.01); *G01R 33/282* (2013.01)

(58) Field of Classification Search
None
See application file for complete search history.

(56) References Cited

U.S. PATENT DOCUMENTS

| | | | | |
|---|---|---|---|---|
| 5,530,140 | A * | 6/1996 | Andersson | A61K 49/20 424/9.3 |
| 2008/0287774 | A1 | 11/2008 | Katz-Brull | |
| 2010/0233096 | A1 * | 9/2010 | Lerche | A61K 49/10 424/9.36 |
| 2011/0243855 | A1 * | 10/2011 | Gisselsson | A61K 49/10 424/9.3 |

FOREIGN PATENT DOCUMENTS

| | | | | |
|---|---|---|---|---|
| SE | WO 2006054903 | A2 * | 5/2006 | ............ A61K 49/06 |
| WO | 96-39367 | A1 | 12/1996 | |
| WO | 98-01766 | A1 | 1/1998 | |
| WO | 98-58272 | A1 | 12/1998 | |
| WO | 99-35508 | A1 | 7/1999 | |
| WO | 2011-124672 | A1 | 10/2011 | |

OTHER PUBLICATIONS

Ardenkjaer-Larsen, Jan H. et al., "Increase in signal-to-noise ratio of > 10,000 times in liquid-state NMR", PNAS, vol. 100, No. 18, 2003, pp. 10158-10163, www.pnas.org/cgi/doi/10.1073/pnas.1733835100.
European Search Report for European application No. 12176269.4, mail date Nov. 30, 2012.
PCT International Search Report and Written Opinion for PCT/EP2013/064121, mail date Sep. 4, 2013.

* cited by examiner

Primary Examiner — Michael G Hartley
Assistant Examiner — Jennifer Lamberski
(74) Attorney, Agent, or Firm — Vivicar Law, PLLC

(57) ABSTRACT

New radical compounds, useful in the field of MRI imaging of formula (I). The radical compounds are in particular new triarylmethyl ("trityl") radicals which can be used as polarizing agents for polarizing a molecule in the DNP process.

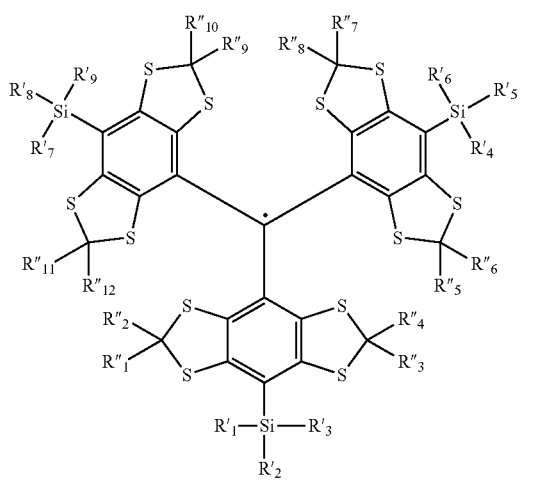

12 Claims, No Drawings

TRIARYLMETHYL RADICALS

CROSS-REFERENCE TO RELATED APPLICATIONS

This application is the national stage application of corresponding international application number PCT/EP2013/064121, filed Jul. 4, 2013, which claims priority to and the benefit of European application no. 12176269.4, filed Jul. 13, 2012, all of which are hereby incorporated by reference in their entirety.

TECHNICAL FIELD

The present invention relates to new radical compounds, useful in the field of MRI imaging. In particular, the radical compounds of the invention are new triarylmethyl ("trityl") radicals which can be used as polarizing agents for polarizing a molecule in the DNP process. The invention further relates to a DNP process which comprises the use of the radicals as polarizing agents.

BACKGROUND OF THE INVENTION

Magnetic Resonance Imaging (MRI) is a non-invasive technique with broad diagnostic value. The technique has gained wide clinical acceptance and is of great importance in diagnostic medicine. However, despite significant technological advancements (increasing field strength and improvement in technology), applications of MRI are limited by an intrinsically low sensitivity.

Some alternatives to enhance its sensitivity have been developed which involve ex-vivo nuclear spin polarisation of agents, prior to administration and subsequent in-vivo measurement of the Magnetic Resonance (MR) signal as disclosed, for instance, in WO 98/01766, WO 98/58272 and WO 99/35508.

In particular, the process of Dynamic Nuclear Polarization (DNP) involves the preparation of a mixture comprising a hyperpolarizable molecule (typically enriched in a non-zero nuclear spin atom, e.g. $^{13}C$) together with a polarizing agent (e.g. a trityl radical). The sample is then frozen at very low temperatures (few ° K) for the polarization process. As successful polarization levels are generally achieved when the mixture upon freezing forms a glass (rather than a crystallized sample), the mixture may thus further comprise a glass-forming agent (e.g. glycerol, DMSO, etc.) to avoid crystallization of the sample.

Once the desired level of polarization is achieved, the sample is rapidly dissolved in an aqueous carrier and administered to a patient, for subsequent MR signal detection. Before administration of the hyperpolarized sample, the polarizing agent (in particular the trityl radical) is preferably removed, at least in part, from the mixture.

The Applicant has however observed that the trityl radicals generally employed in the art are relatively soluble in the aqueous preparation for the administration of the sample, which may render their separation from the mixture relatively cumbersome and/or only partial.

The Applicant has now found new trityl radicals which are substantially insoluble in water, thus allowing an effective separation of the radical from a hyperpolarized sample.

SUMMARY OF THE INVENTION

An aspect of the invention relates to a radical of formula (I)

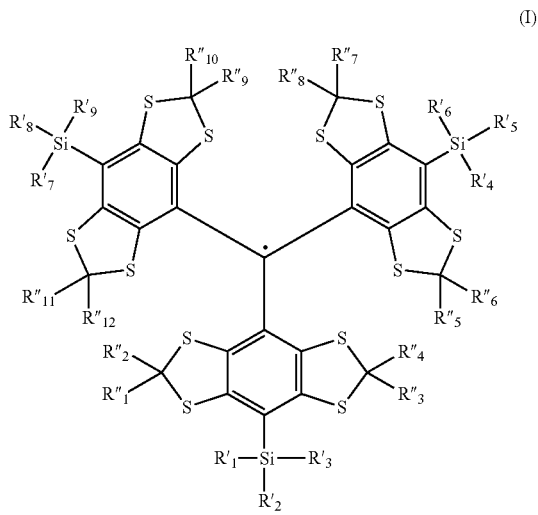

(I)

Wherein
each $R'_1$-$R'_9$ independently represents:
a straight or branched $C_1$-$C_6$ alkyl group, optionally substituted with an aromatic group; or
a group of formula —$(CH_2)_n$-A-R''', wherein:
n is 1, 2 or 3;
A is —S—, —O—, —CO—, —CO—O—, —CO—NH—, —SO—, —SO$_2$— or —SO$_2$—NH—; and
R''' is hydrogen or a straight or branched $C_1$-$C_4$ alkyl group;
each $R''_1$-$R''_{12}$ independently represents:
a straight or branched $C_1$-$C_6$ alkyl group; or
a group of formula —$(CH_2)_n$—B—R''', wherein:
n is 1, 2 or 3;
B is —S—, —O—, —CO—, —CO—O— or —CO—NH—; and
R''' is hydrogen or a straight or branched $C_1$-$C_4$ alkyl group.

Preferably, when A and/or B in the above formula represent a group —CO—O—, then R''' is not hydrogen.

According to an embodiment of the invention, one or more of the hydrogen atoms of the groups R' and/or R'' are deuterium. Preferably, all the hydrogen atoms of the groups R' and/or R'' are deuterium.

Preferably each $R'_1$-$R'_9$ independently represents a straight or branched $C_1$-$C_6$ alkyl group, optionally substituted with an aromatic group or a group —$(CH_2)_n$-A-R''', where n and A are as above defined and R''' is a straight or branched $C_1$-$C_4$ alkyl.

Preferably each $R''_1$-$R''_{12}$ independently represents a straight or branched $C_1$-$C_6$ alkyl group or a group —$(CH_2)_n$—B—R''', where n and B are as above defined and R''' is a straight or branched $C_1$-$C_4$ alkyl.

According to a particularly preferred embodiment each $R'_1$-$R'_9$ and each $R''_1$-$R''_{12}$ independently represent a straight or branched $C_1$-$C_6$ alkyl group.

The term "aromatic group" includes any 5-7 membered carbocyclic or heterocyclic aromatic ring, said ring being optionally substituted (e.g. with C1-C4 alkyl) and/or optionally carrying one or more fused carbocyclic or heterocyclic rings. Preferably the aromatic group is phenyl or naphtyl, optionally substituted with C1-C4 alkyl chain.

Another aspect of the invention relates to a DNP preparation which comprises a $^{13}$C-labelled compound in admixture with a radical of formula I.

A further aspect of the invention relates to a method for preparing a polarized sample for MR imaging which comprises:
  submitting a mixture comprising a $^{13}$C-labelled compound and a radical of formula (I) to DNP, to obtain a polarized sample;
  dissolving said mixture in an aqueous carrier
  removing the radical of formula (I) from the polarized sample.

A still further aspect of the invention relates to a method for MR imaging which comprises:
  preparing a polarized sample as above described;
  administering said polarized sample to a subject; and
  detecting a MR signal from said subject.

DETAILED DESCRIPTION OF THE INVENTION

The radicals according to the present invention can be advantageously used for the preparation of a mixture which undergoes the DNP process.

In particular, the radicals of the invention act as effective polarizing agents when admixed with a MR active compound, i.e. a compound comprising a non-zero nuclear spin atom. Advantageously, they can be quantitatively separated from the polarized mixture at the end of the DNP process, when the polarized mixture is dissolved in water, before administration thereof.

In general, while a partial removal of the radical may in some instance be acceptable, under clinical practice it is nevertheless desirable to quantitatively remove it from the mixture to be administered, to avoid the administration of non-negligible amounts of radical to a subject. In particular it is desirable that the concentration of the radical in the administered mixture is below 200 μM, preferably below 50 μM and even more preferably below 10 μM.

The radical of the invention, because of its substantially low solubility in water, precipitates quantitatively once the polarized mixture is contacted with water and can be removed from the solution according to conventional techniques, such as filtration.

As used herein, the expression "low solubility in water", particularly when referred to the radicals of the invention, means that the compound has a solubility in water of less than 15 mg/L, preferably of less than 10 mg/L, more preferably of less than 5 mg/L and even more preferably of less than 1.5 mg/L.

Preferably, the radical of the invention is formed by three identical groups, as illustrated in formula II:

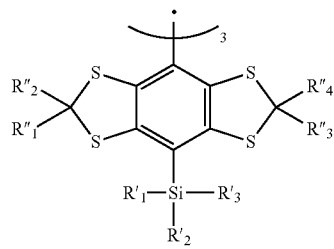

(II)

where R'$_1$-R'$_3$ and R"$_1$-R"$_4$ have the same meanings as above defined.

According to particularly preferred embodiments, the radical according to the invention is selected among the following compounds:

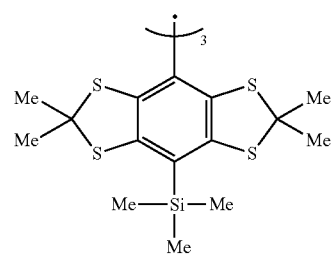

IIa

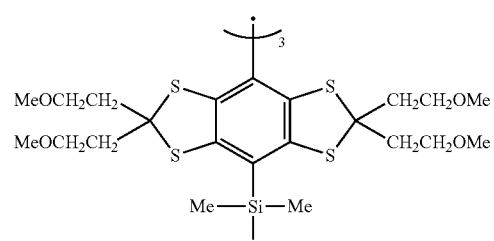

IIb

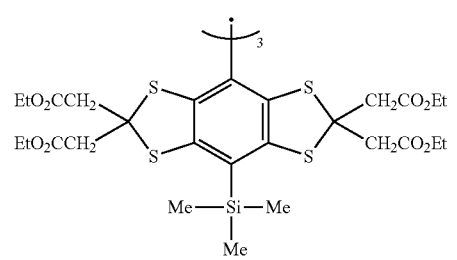

IIc

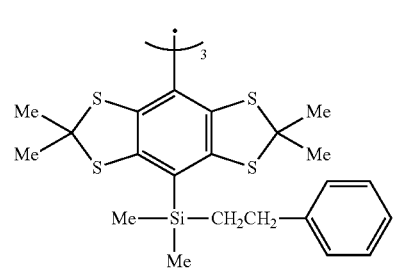

IId

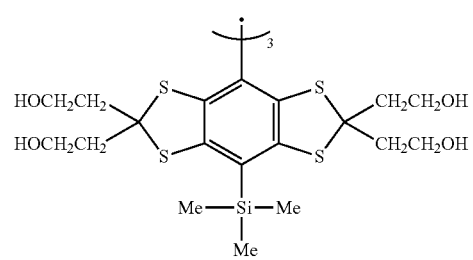

IIe wherein each of the methyl, ethyl or phenyl group is preferably deuterated.

The radicals according to the invention can be prepared according to the following schematic reaction pathway(s).

In particular, the monomer forming the trityl radical can be prepared as follows:

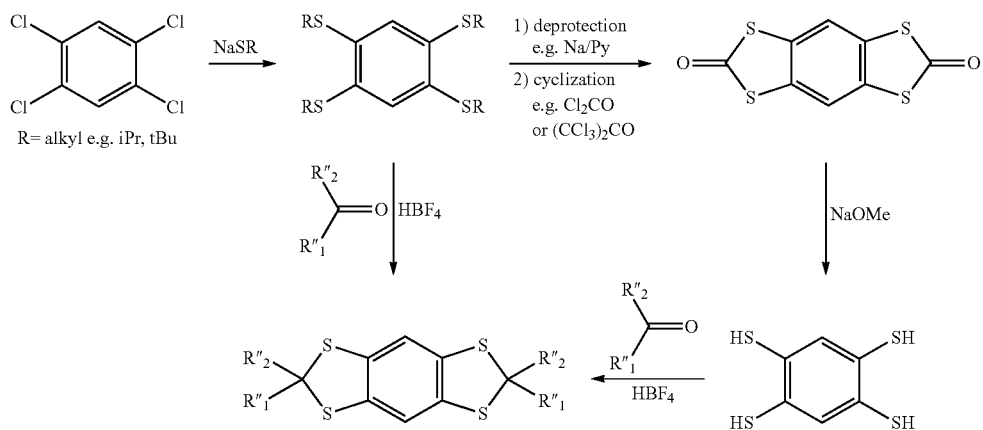

The so obtained monomer can then be converted into the respective trityl radical according to the following general reaction scheme:

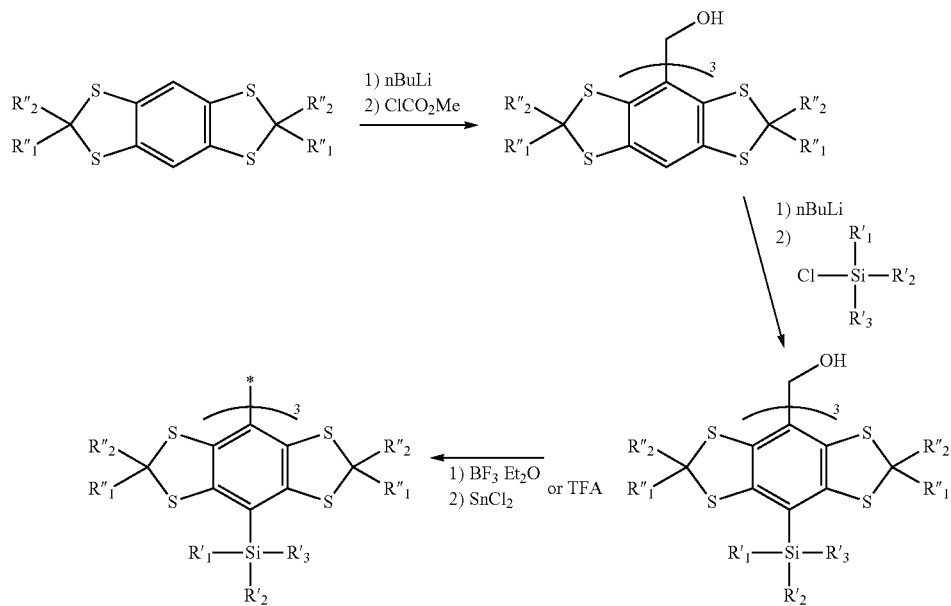

The radicals of the invention can be admixed together with a desired MR active compound in a mixture which can be hyperpolarized according to conventional methods.

As defined herein, "MR active compound" comprises within its meaning compounds containing non-zero nuclear spin nuclei capable of exhibiting a long T1 relaxation time. Long T1 relaxation times are to be intended as time values sufficiently long to allow an effective detection of the signal once the compound is administered into a subject.

According to an embodiment of the invention, substituents R' and R" in formula I can be selected in order to provide a solubility of the radical, in the preparation containing the MR active compound to be polarized, that is sufficient for allowing an effective DNP process. In preferred embodiments, the substituents R' and R" in the radicals of formula (I) are selected in order to contain similar chemical groups as the MR active compound to be polarized. Thus, for instance, when the MR active compound is a carboxylic ester, one or more of the R' and/or R" groups may be —$CH_2CH_2OCH_3$ or —$CH_2CH_2OCH_2CH_2OCH_3$. Alternatively, when a radical having a polarity substantially different from the one of the MR active compound is used, the radical can advantageously be dissolved in advance into a suitable solvent (compatible also with the MR active compound in liquid form), in order to increase the mixing between the radical and the MR active compound. For instance, compound IIa can advantageously be dissolved in Crown ether before admixing it with ethylacetoacetate. Preferably, the solvent used for the preliminary dissolution of the radical is also a glass forming agent.

Preferably, the MR active compound admixed with the radical of formula I in the DNP preparation is enriched with non-zero nuclear spin nuclei, such as $^{13}C$, $^{19}F$ and/or $^{15}N$ nuclei even more preferably, enriched with $^{13}C$.

The term "enriched" means that the concentration of the non-zero spin nuclei in the compound is above the typical value of natural abundance of said nuclei, preferably above at least 10% of natural abundance, more preferably above at least 25%, and even more preferably above at least 75% of its natural abundance and most preferably above at least 90% of its natural abundance. The enrichment will in particular be concentrated on an atom position, for which a chemical transformation of the molecule, or a chemical or magnetic changes of the environment of the molecule, will be measurable as a change of its chemical shift. Said non-zero nuclei confer to the substrate a T1 relaxation time of at least 5 seconds (indicated with s), preferably of at least 10 s, preferably of at least 20 s, preferably of at least 30 s, and even more preferably of at least 40 s, measured in a solution subjected to a magnetic fields of from about 0.5 mT to about 20 T (Tesla). The enrichment may include either selective enrichments of one or more sites within the molecule or uniform enrichment of all sites.

The MR active compound can be either in the form of a MR agent, which is thus administered as such after the DNP process and dissolution of the polarized sample; alternatively, the MR active compound can be in the form of a precursor of a MR agent, which is transformed in the desired MR agent upon dissolution in water, as illustrated for instance in WO 2011/124672. According to a preferred embodiment, the radicals of the invention can be advantageously admixed with an ester precursor of an MR active substrate, as disclosed in the above cited WO 2011/124672.

As defined herein, "MR agent" identifies a hyperpolarized molecule which, upon administration in a subject and when exposed to a uniform magnetic field (also known as "primary magnetic field") with radiation at a frequency selected to excite nuclear spin transitions in said molecule provides a MR signal.

As the signal of any hyperpolarized molecule decays due to spin relaxation, the final hyperpolarized MR agent, particularly when in solution, shall maintain its polarization for a sufficiently long period of time, in order to allow the imaging procedure to be carried out within a relatively comfortable frame of time. Preferably, the T1 value of the MR agent shall thus be of at least 5 seconds or higher, preferably of 10 s seconds or higher, more preferably at least 30 s seconds and even more preferably of 50 s seconds or higher. Particularly preferred are those compounds for which the T1 value is of 70 s seconds or higher, and even more particularly preferred are those having a T1 value of 100 s seconds or higher. Said T1 values are referred to values measured typically at a field strength of from 0.5 mT to 20 T and at a temperature of from 25° C. to 70° C., in particular at a field strength of 1.5-3 T and at a temperature of 37° C. When outside the body, said T1 values are generally measured at a field strength of 0.5 mT and at a temperature of 60° C. If desired, the non-zero spin nuclei in the MR active compound can be directly linked to one or more Deuterium atom (see e.g. US 2008/0287774 A1, herein included by reference). Typically, the MR active compounds of a hyperpolarized mixture according to the invention are in particular capable of exhibiting a change in chemical shift in response of a change of physiological conditions (e.g. changes in the pH, $pO_2$, $pCO_2$, redox potential, temperature or ionic concentrations in the vascular system) or a consequence of metabolic activities, such as cellular uptake, cytosolic reactions such as transaminase reactions (comprising amino acids e.g. aspartate and keto acids e.g. oxaloacetate) and glycolysis (comprising carbohydrates e.g. glucose), mitochondrial reactions such as TCA cycle reactions (comprising molecules which are hydrated e.g cis-acotinate), redox reactions (comprising ketobodies e.g. acetoacetate) or betaoxidations (comprising short and medium chain fatty acids e.g. butyrate).

Preferred MR agents will for instance exhibit a chemical shift difference of more than 1.5 ppm for quaternary carbon, 2.1 ppm for deuterate methine, 4.2 ppm for deuterated methylene, and 5.4 ppm for deuterated methyl groups, at a field of 3T.

Optionally, the DNP preparation may further contain a glass-forming agent, in order to provide a solid sample for the DNP preparation in glass form. Examples of suitable glass forming agents include, for instance, glycerol, ethanol, crown ethers or DMSO The amount of glass forming agent in the DNP preparation may vary from 10% to 75% (with respect to the total weight), preferably from 10% to 50% even more preferably from 10% to 25%.

The DNP preparation undergoes then to the process of dynamic nuclear polarization, according to methodologies known in the art (see e.g. Ardenkjær-Larsen et a, PNAS, 2 Sep. 2003, Vol 100, no. 18 pp. 10158-10163). For instance, the DNP process is performed at a relatively high magnetic field (typically from about 3 to about 8 Tesla, and at low temperatures (typically lower than 100° K, more preferably lower than 10° K, e.g. from 0.5 to 4° K, even more preferably from 0.5 to 2° K); the sample is then subjected to microwave irradiation to achieve a level of polarization of the sample of at least 1%, preferably of at least 5% and even more preferably of at least 10%, where polarization is defined by the following equation:

$$P = \frac{N\alpha - N\beta}{N\alpha + N\beta}$$

wherein;
$N\alpha$ is the number of spins in nuclear spin state $\alpha$; and
$N\beta$ is the number of spins in nuclear spin state $\beta$.

In the practice, a container containing the DNP preparation is introduced into a polarizing device comprising a cryostat (e.g. with liquid He cooling system), means for producing the desired magnetic field and a microwave generator.

Advantageously, dissolving means are connected with the polarizing device, in order to rapidly dissolve the polarized mixture once the desired level of polarization has been achieved. Preferably, in case the polarized sample has to be administered to a patient, the polarizing device further contains means for recovering the dissolved sample and providing it to an injection system for administration thereof.

The obtained solution is then subjected, before injection thereof, to a separation step in order to remove, at least in part, the radical from the DNP preparation. The radical of formula I can be removed for instance by mechanical filtration or sorbent filtration. Preferably the separation of the radical is effected by mechanical filtration, e.g. with a small pore filter (e.g with pore sizes from about 0.1 μm to about 5 μm, preferably from about 0.45 μm to about 2.5 μm). The filter can be for instance a fritted glass filter or a membrane filter. The filter can be made from any suitable material, preferably hydrophilic material, such as, for instance, polyvinylidene difluoride (PVDF). Because of its low solubility in water, the radical of formula I can be quantitatively removed from the mixture to be administered. In particular, less than 10% of the total amount of radical remains in the mixture to be administered, preferably less than 5% and even more preferably less than 1%.

After removal of the radical, the polarized sample can thus be administered to a patient, in order to proceed with the MR imaging thereof. In particular, the imaging method comprises the detection of an MR signal from the MR active compound or from a metabolite thereof.

According to a preferred embodiment, the removal of the radical is effected concurrently with the administration of the polarized sample. For instance, the polarized sample can be administered by means of a syringe provided at its exit with a suitable filter (of hydrophilic material) for separating the radical.

The following examples will help to further illustrate the invention.

EXAMPLES

Materials

The following materials are employed in the subsequent examples:

| | |
|---|---|
| Radical 1 | (tris{8-carboxyl-2,2,6,6-tetramethyl-benzo(1,2-d:4,5-dS)bis(1,3)dithiole-4-yl}methyl sodium salt) |
| TMST radical | (tris{8-trimethylsilyl-2,2,6,6-tetramethyl-benzo(1,2-d:4,5-dS)bis(1,3)dithiole-4-yl}methyl |
| 15-Crown-5 | 1,4,7,10,13-Pentaoxacyclopentadecane |

Example 1

Preparation of TMST Radical

1a) Preparation of 1,2,4,5-tetra-tert-butylthiobenzene (Compound 1a)

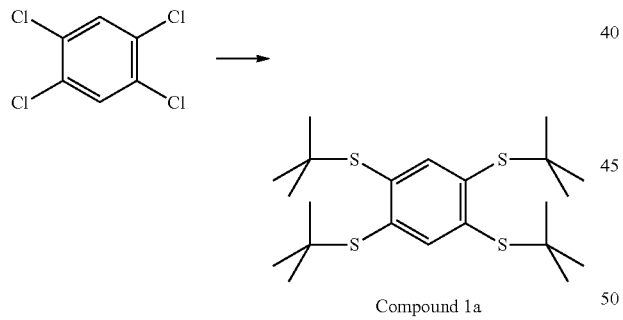

Compound 1a

Sodium (9.3 g, 0.18 mol) was added to a degassed solution of 2-methyl-2-propanethiol (20.9 mL, 0.18 mol) in dry DMF (105 mL), under stirring at 0° C. in nitrogen atmosphere. The mixture was allowed to reach room temperature (RT, 20-25° C.) and stirred overnight. 1,2,4,5-Tetrachlorobenzene (8.0 g, 0.037 mol) was then added and the resulting mixture was stirred at RT for 2 h and then gently refluxed for 18 h. After cooling at RT, the reaction mixture was poured over ice (100 g), the precipitate was removed by filtration, washed with water, and dried to give 11.0 g of the title compound as an off-white powder.

$^1$H NMR (600 MHz, CDCl$_3$): δ 1.36 (s, 36H), 7.94 (s, 2H).
$^{13}$C NMR (150 MHz, CDCl$_3$): δ 31.4, 48.3, 139.5, 144.9.
MS (ESI): [M+H]$^+$ 430.7 (observed), 431.2 (calcd).

1b) Preparation of 2,2,6,6-Tetramethylbenzo[1,2-d;4,5-']bis[1,3]dithiole (compound 1b)

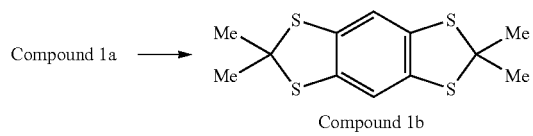 [SMILES: CC1(C)Sc2cc3c(cc2S1)SC(C)(C)S3]

Dry acetone (11 mL) was added to a suspension of compound 1a (10.0 g, 0.023 mol) in dry toluene (90 ml), followed by 54% HBF$_4$ in ether (6.3 mL, 0.046 mol), at RT. The mixture was stirred at RT for 4 h and then heated to reflux for 18 h. After being cooled at RT, the resulting brown mixture was treated with saturated aqueous NaHCO$_3$ (100 mL) and the crude product was extracted with diethyl ether (3×100 mL). The organic phases were dried over Na$_2$SO$_4$ and concentrated under vacuum. The resulting yellow solid was triturated with methanol and petroleum ether to give 4.91 g of the title compound as an off-white powder.

$^1$H NMR (600 MHz, CDCl$_3$): δ 1.88 (s, 12H), 7.02 (s, 2H).
$^{13}$C NMR (150 MHz, CDCl$_3$): δ 31.4, 65.9, 116.9, 135.9.

1c) Preparation of Bis-(2,2,6,6-tetramethyl-benzo[1,2-d;4,5-d']bis[1,3]dithiol-4-yl)methanone (Compound 1c) and Tris-(2,2,6,6-tetramethyl-benzo[1,2-d;4,5-d']bis[1,3]dithiol-4-yl)methanol (Compound 1d)

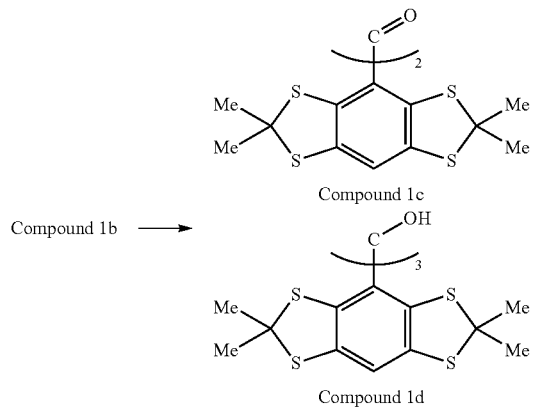

4.2 mL (0.0105 mol) of n-butyl lithium 2.5 M in hexane were added to a solution of Compound 1b (3.0 g, 0.0105 mol) in dry diethyl ether (115 mL), at RT under argon atmosphere. The orange solution was stirred at RT for 4 h. Methyl chloroformate (0.32 mL, 0.0042 mol) was dissolved in dry diethyl ether (35 mL) and added drop wise to the solution over 2 h at RT. The resulting orange solution was stirred at RT over 40 h. Saturated aqueous NaHCO$_3$ was added (100 mL), and the organic phase was separated. The aqueous phase was extracted again with diethyl ether (2×80 mL). The combined organic phases were dried over Na$_2$SO$_4$, and evaporated to afford a mixture of compound 1c and compound 1d together with the starting material. The mixture was purified by flash chromatography on silica gel eluting first with hexane (to remove compound 1b) and then with 20:1 hexane-ethyl acetate to recover compound 1c (1.2 g) and a mixed fraction of compounds 1c and compound 1d (0.40 g).

$^1$H NMR (600 MHz, CDCl$_3$): δ 1.78 (s, 24H), 7.17 (s, 2H).

$^{13}$C NMR (150 MHz, CDCl$_3$): δ 31.2, 65.5, 119.4, 127.4, 137.7, 137.8, 193.6.

MS (ESI): [M+H]$^+$ 598.6 (observed), 598.97 (calcd).

1d) Preparation of Tris-(2,2,6,6-tetramethyl-benzo[1,2-d;4,5-d']bis[1,3]dithiol-4-yl)methanol (Compound 1d)

Compound 1b+Compound 1c→Compound 1d 2.5 mL (0.0063 mol) of n-butyl lithium 2.5 M in hexane were added to a solution of compound 1b (1.8 g, 0.0063 mol) in dry diethyl ether (70 mL) at RT. The solution was stirred at RT for 4 h. Then, compound 1c (1.0 g, 0.0017 mol) was added and the resulting orange mixture was stirred at RT for 40 h. Saturated aqueous NaHCO$_3$ was added (50 mL), and the organic phase was separated. The aqueous phase was extracted again with diethyl ether (2×50 mL). The combined organic phases were dried over Na$_2$SO$_4$, and evaporated. The mixture was purified by flash chromatography on silica gel by eluting first with hexane and then with 50:1 hexanes-ethyl acetate, to recover the desired compound 1d (1.4 g).

$^1$H NMR (600 MHz, CDCl$_3$): δ 1.67 (s, 9H), 1.71 (s, 9H), 1.80 (s, 9H), 1.81 (s, 9H), 6.22 (s, 1H), 7.17 (s, 3H).

$^{13}$C NMR (150 MHz, CDCl$_3$): δ 27.7, 29.2, 32.3, 34.9, 63.4, 64.2, 83.7, 118.3, 131.9, 137.3, 137.8, 138.3, 139.2.

1e) Preparation of Tris-(8-trimethylsilyl-2,2,6,6-tetramethylbenzo[1,2-d;4,5-d']bis[1,3]dithiol-4-yl)methanol (compound 1e)

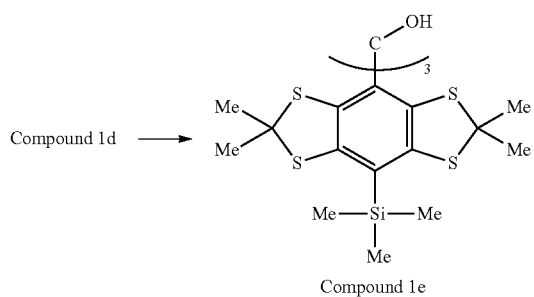 [SMILES: CC1(C)Sc2c(CO)c3c(c([Si](C)(C)C)c2S1)SC(C)(C)S3]

Compound 1d (0.15 g, 0.17 mmol) was dissolved in dry diethyl ether (5 mL) and tetrametyhlethylendiamine (0.26 mL, 1.69 mmol) was added under argon atmosphere. The mixture was cooled at 0° C., n-butyl lithium 2.5 M in hexane (0.68 mL, 1.69 mmol) was added drop wise over 10 min and the mixture was left to reach RT. After stirring for 3 h at RT, the resulting brown solution was added drop wise at 0° C. to a solution of trimethylchlorosilane (0.65 mL, 5.08 mmol) in diethyl ether (2 mL). The solution was stirred at RT for 4 h and the formation of a white solid was observed. The solid was filtered off, washed with diethyl ether and the organic solution was concentrated under vacuum. The crude product was purified by gravimetric chromatography on silica gel eluting with 15:1 hexanes-ethyl acetate to afford the title compound as an orange powder (0.12 g).

$^1$H NMR (600 MHz, CDCl$_3$): δ 0.47 (s, 27H), 1.64 (s, 9H), 1.66 (s, 9H), 1.78 (s, 9H), 1.79 (s, 9H), 6.52 (s, 1H).

$^{13}$C NMR (150 MHz, CDCl$_3$): δ 2.4, 27.1, 29.0, 31.9, 34.2, 61.0, 61.4, 84.5, 129.8, 132.9, 138.5, 104.0, 143.6, 144.4.

MS (ESI): [M−H]$^−$ 1098.9 (observed), 1099.1 (calcd).

1f) Tris-(8-trimethylsilyl-2,2,6,6-tetramethylbenzo[1,2-d;4,5-d']bis[1,3]dithiol-4-yl)methyl (TMST Radical)

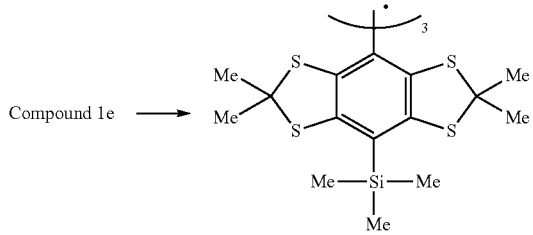 [SMILES: Cc1c2c(c([Si](C)(C)C)c3c1SC(C)(C)S3)SC(C)(C)S2]

BF$_3$.Et$_2$O (19 μL, 0.15 mmol) was added to a stirred solution of compound 1e (21 mg, 0.019 mmol) in dichloromethane (2.5 mL), at 0° C. After stirring for 1 h, the resulting dark green solution was treated with a solution of SnCl$_2$ (6.0 mg, 0.032 mmol) in tetrahydrofuran (1 mL). After 15 min, saturated aqueous KH$_2$PO$_4$ (5 mL) was added. The organic layer was separated, dried over Na$_2$SO$_4$, and concentrated under vacuum to give the title radical as a dark green solid (19 mg).

MS (ESI): [M−H]$^−$ 1083.2 (observed), 1083.1 (calcd).

Example 2

Comparative

DNP Preparation, Polarization Build-Up and Dissolution of Ethylacetoacetate with Radical 1

Radical 1 (1.50 mg, 1.4 μmol) was dissolved in 15-Crown-5 (60.5 μl, 67.2 mg) to make a 24 mM solution. To 30 μl (33.7 mg) of this solution was added 1,3-$^{13}$C$_2$ ethylacetoacetate (10.5 mg, 79 μmol, 158 μmol $^{13}$C). The radical 1 concentration in the mixture was 18 mM.

43 mg of the composition prepared above were transferred from the Eppendorf tube to a sample cup and the sample cup was inserted into a DNP polarizer. The composition was polarised under DNP conditions at 1.2 K in a 3.35 T magnetic field under irradiation with microwave (93.900 GHz). The calculated solid-state polarization was 17% and the polarization build-up constant was 900 s.

The sample was dissolved in 6 ml 40 mM phosphate buffer pH 7.3+100 mg/l EDTA. A time series of 1D 13C-NMR spectra were recorded with a total delay between the pulses of 3 s. The liquid state polarization was 14% after 12 s transfer time. The pH was 7.3 in the dissolved sample.

The radical 1 does not precipitate in water dissolution and cannot be removed by mechanical filtration Example 3

DNP Preparation, Polarization Build-Up and Dissolution of Ethylacetoacetate with TMST Radical TMST radical (1.10 mg, 1.0 μmol) was dissolved in 15-Crown-5 (40.5 μl, 45.1 mg) to make a 24 mM solution. To 30 μl (33.5 mg) of this solution was added 1,3-$^{13}$C$_2$ ethylacetoacetate (10.5 mg, 79 μmol, 158 μmol $^{13}$C). The TMST radical concentration in the mixture was 18 mM.

43 mg of the composition prepared above were transferred from the Eppendorf tube to a sample cup and the sample cup was inserted into a DNP polarizer. The composition was polarised under DNP conditions at 1.2 K in a 3.35 T magnetic field under irradiation with microwave (93.875 GHz). The calculated solid-state polarization was 18% and the polarization build-up constant was 1700 s.

The sample was dissolved in 6 ml 40 mM phosphate buffer pH 7.3+100 mg/l EDTA. A time series of 1D 13C-NMR spectra were recorded with a total delay between the pulses of 3 s. The liquid state polarization was 15% after 12 s transfer time. The pH was 7.3 in the dissolved sample. The sample was filtered through a syringe filter (Acrodisk 25 mm PVDF filter, 0.45 μm pore size). Filtration of the full volume was completed in <3 s. The filtered sample had no detectable absorbance at 462 nm as verified with UV-Vis spectroscopy. Since the high extinction coefficients of the trityl radicals allow reliable determination of concentration down to approximately 1-1.5 μM, the concentration in the filtrate was below these values. The radical was removed to >99%.

The invention claimed is:

1. A radical of formula (I)

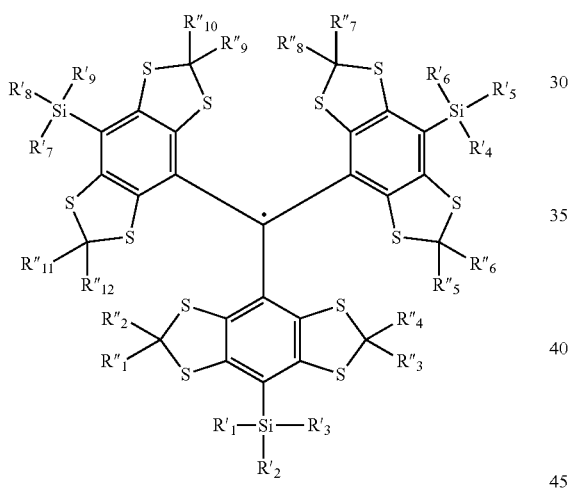

(I)

wherein
each $R'_1$-$R'_9$ independently represents:
a straight or branched $C_1$-$C_6$ alkyl group, optionally substituted with an aromatic group; or
a group of formula —$(CH_2)_n$-A-R''', wherein:
n is 1, 2 or 3;
A is —S—, —O—, —CO—, —CO—O—, —CO—NH—, —SO—, —SO$_2$— or —SO$_2$—NH—; and
R''' is hydrogen or a straight or branched $C_1$-$C_4$ alkyl group;
each $R''_1$-$R''_{12}$ independently represents:
a straight or branched $C_1$-$C_6$ alkyl group; or
a group of formula —$(CH_2)_n$—B—R''', wherein:
n is 1, 2 or 3;
B is —S—, —O—, —CO—, —CO—O— or —CO—NH—; and
R''' is hydrogen or a straight or branched $C_1$-$C_4$ alkyl group.

2. The radical of claim 1 wherein when A and/or B in the above formula represent a group —CO—O—, then R''' is not hydrogen.

3. The radical according to claim 1 wherein one or more of the hydrogen atoms of the groups R' and/or R'' are deuterium.

4. The radical according to claim 1 wherein each $R'_1$-$R'_9$ independently represents a straight or branched $C_1$-$C_6$ alkyl group, optionally substituted with an aromatic group or a group —$(CH_2)_n$-A-R''', where n and A are as defined in claim 1 and R''' is a straight or branched $C_1$-$C_4$ alkyl.

5. The radical according to claim 1 wherein each $R''_1$-$R''_{12}$ independently represents a straight or branched $C_1$-$C_6$ alkyl group or a group —$(CH_2)_n$—B—R''', where n and B are as defined in claim 1 and R''' is a straight or branched $C_1$-$C_4$ alkyl.

6. The radical according to claim 1 which has a formula selected from the group consisting of:

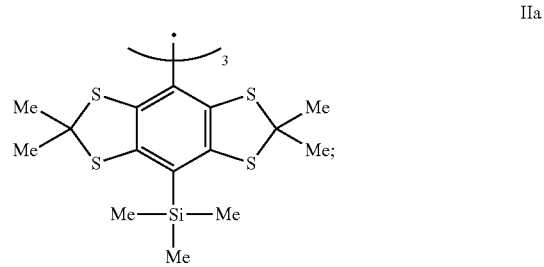

IIa

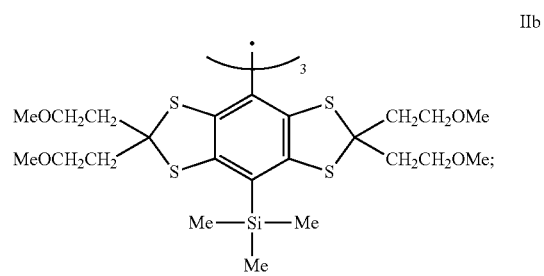

IIb

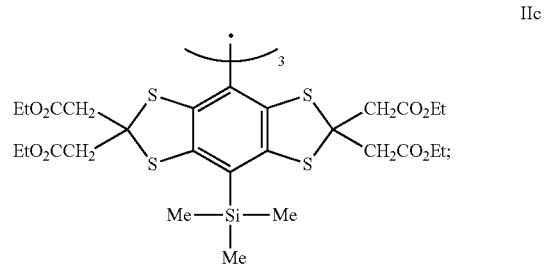

IIc

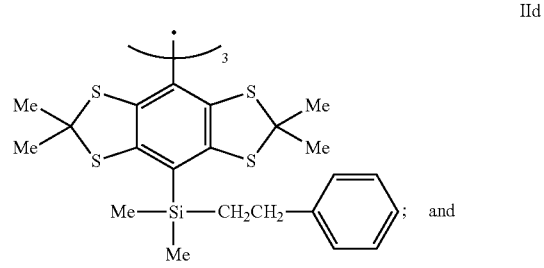

IId

; and

-continued

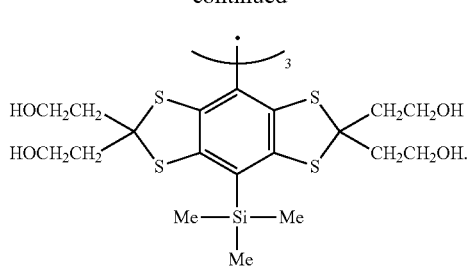

IIe

7. A dynamic nuclear polarization (DNP) preparation which comprises a $^{13}$C-labelled compound in admixture with a radical of claim 1.

8. The DNP preparation of claim 7 wherein said $^{13}$C-labelled compound is an ester precursor of an magnetic resonance (MR) agent.

9. A DNP preparation which comprises a $^{13}$C-labelled compound in admixture with a radical of claim 3.

10. A DNP preparation which comprises a $^{13}$C-labelled compound in admixture with a radical of claim 6.

11. A method for preparing a polarized sample for MR imaging which comprises:
submitting a mixture comprising a $^{13}$C-labelled compound and a radical according to claim 1 to DNP, to obtain a polarized sample;
dissolving said mixture in an aqueous carrier; and
removing the radical from the polarized sample.

12. A method for preparing a polarized sample for MR imaging which comprises:
submitting a mixture comprising a $^{13}$C-labelled compound and a radical according to claim 6 to DNP, to obtain a polarized sample;
dissolving said mixture in an aqueous carrier; and
removing the radical from the polarized sample.

\* \* \* \* \*